United States Patent [19]

Obata et al.

[11] Patent Number: 5,039,692

[45] Date of Patent: Aug. 13, 1991

[54] PHENOXYALKYLAMINE DERIVATIVES, AND INSECTICIDES, ACARICIDES AND FUNGICIDES

[75] Inventors: Tokio Obata; Katsutoshi Fujii; Toshinobu Tanaka; Akira Ooka; Shoji Shikita, all of Ube, Japan

[73] Assignee: Ube Industries, Ltd., Ube, Japan

[21] Appl. No.: 539,965

[22] Filed: Jun. 15, 1990

[30] Foreign Application Priority Data

Jun. 26, 1989 [JP] Japan .................................. 1-160949

[51] Int. Cl.$^5$ ................... A01N 43/56; C07D 231/14; C07D 231/16
[52] U.S. Cl. ..................................... 514/406; 548/377; 548/378
[58] Field of Search ................ 548/377, 378; 514/406

[56] References Cited

U.S. PATENT DOCUMENTS 4,782,074 11/1988 Spatz ..................................... 548/378

Primary Examiner—Robert W. Ramsuer
Attorney, Agent, or Firm—Frishauf, Holtz, Goodman & Woodard

[57] ABSTRACT

There are disclosed a phenoxyalkylamine derivative represented by the formula:

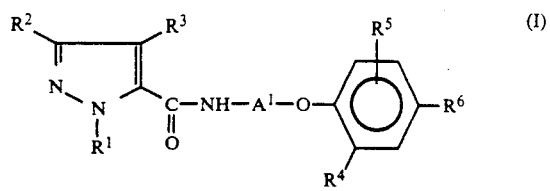

wherein $A^1$ represents an alkylene group having 2 to 5 carbon atoms, $R^1$ and $R^2$ each represent hydrogen atom or a lower alkyl group having 1 to 5 carbon atoms, $R^3$, $R^4$ and $R^5$ each represent hydrogen atom, an alkyl group having 1 to 5 carbon atoms or a halogen atom, $R^6$ represents hydrogen atom, an alkyl group having 1 to 5 carbon atoms, an alkenyl group having 3 to 5 carbon atoms or a group $-A^2-X-R^7$, $A^2$ represents an alkylene group having 1 to 5 carbon atoms, X represents oxygen atom or sulfur atom, $R^7$ represents a lower alkyl group having 1 to 5 carbon atoms, an alkenyl group having 3 to 5 carbon atoms, an alkynyl group having 3 to 5 carbon atoms or a substituted or unsubstituted aralkyl group, and an insecticide, an acaricide and a fungicide for agriculture and horticulture, which comprises a carrier and the above phenoxyalkylamine derivative represented as the active ingredient.

32 Claims, No Drawings

PHENOXYALKYLAMINE DERIVATIVES, AND INSECTICIDES, ACARICIDES AND FUNGICIDES

BACKGROUND OF THE INVENTION

1. Field of the Invention

This invention relates to phenoxyalkylamine derivatives, and insecticides, acaricides and fungicides for agriculture and horticulture containing said derivatives as the active ingredient.

2. Background Information

A large number of phenoxyalkylamine derivatives as agricultural chemicals have been known in the art. For example, Japanese Provisional Patent Publications No. 17123/1979, No. 76803/1980 and No. 76804/1980 reported quinazoline derivatives, Japanese Provisional Patent publication No. 108806/1980 pyridopyrimidine derivatives, Japanese Provisional Patent Publications No. 42387/1984 thienopyrimidine derivatives, Japanese Provisional Patent Publications No. 36666/1984, No. 36667/1984, No. 286373/1986 and No. 67/1987 pyrimidine derivatives.

However, there has been reported nothing about pyrazolecarboxamide derivatives such as the compounds of the present invention at all. Therefore, also no activity as agricultural chemical has been known.

The present inventors have investigated intensively in order to obtain compounds having excellent insecticidal, acaricidal, fungicidal activities, and consequently found that the compounds of the present invention have excellent insecticidal, acaricidal activities and fungicidal activity for agriculture and horticulture, to accomplish the present invention.

SUMMARY OF THE INVENTION

The present invention is a phenoxyalkylamine derivative represented by the following formula:

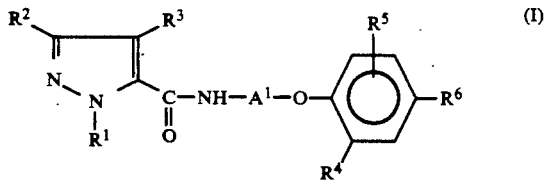

wherein $A_1$ represents an alkylene group having 2 to 5 carbon atoms, $R^1$ and $R^2$ each represent hydrogen atom or a lower alkyl group having 1 to 5 carbon atoms, $R^3$, $R^4$ and $R^5$ each represent hydrogen atom, an alkyl group having 1 to 5 carbon atoms or a halogen atom, $R^6$ represents hydrogen atom, an alkyl group having 1 to 5 carbon atoms, an alkenyl group having 3 to 5 carbon atoms or a group $-A^2-X-R^7$, $A^2$ represents an alkylene group having 1 to 5 carbon atoms, X represents oxygen atom or sulfur atom, $R^7$ represents a lower alkyl group having 1 to 5 carbon atoms, an alkenyl group having 3 to 5 carbon atoms, an alkynyl group having 3 to 5 carbon atoms or a substituted or unsubstituted aralkyl group, and an insecticide, an acaricide and a fungicide for agriculture and horticulture containing said derivative as the active ingredient.

DESCRIPTION OF THE PREFERRED EMBODIMENTS

In the above formula (I), the lower alkyl group having 1 to 5 carbon atoms represented by $R^1$ to $R^7$ is a straight or branched alkyl group, including methyl, ethyl, propyl, isopropyl, butyl, isobutyl, sec-butyl, t-butyl, amyl, isoamyl and sec-amyl groups.

As the halogen atom represented by $R^3$ to $R^5$, fluorine, chlorine, bromine and iodine may be included.

As the alkenyl group having 3 to 5 carbon atoms represented by $R^6$ or $R^{7,}$ there may be included straight or branched alkenyl groups, such as allyl, 1- or 2-butenyl, 1- or 2-methylallyl, 2-pentenyl and isoprenyl groups.

As the alkynyl group having 3 to 5 carbon atoms represented by $R^{7,}$ there may be mentioned a straight or branched alkynyl group such as propargyl, 1-propinyl and 2-butynyl gruops.

As the substituted or unsubstituted aralkyl group represented by $R^{7,}$ benzyl, 1- or 2-phenethyl, 4-chlorobenzyl, 4-fluorobenzyl, 4-methylbenzyl, 3,4-dichlorobenzyl and 2,4-difluorobenzyl groups may be included.

As the alkylene group having 2 to 5 carbon atoms represented by $A^1$, there may be included straight or branched alkylene groups, such as ethylene, trimethylene, 1- or 2-methylethylene, tetramethylene, 1- or 2-ethylethylene, dimethylmethylene and pentamethylene groups.

As the alkylene group having 1 to 5 carbon atoms represented by $A^{2,}$ other than those mentioned for the alkylene group having 2 to 5 carbon atoms in the previous paragraph, straight or branched alkylene groups such as a methylene group may be included. $R^1$ is preferably methyl. $R^2$ is preferably methyl, ethyl or propyl group. $R^3$ is preferably chlorine and bromine atom. $R^4$ and $R^5$ are preferably hydrogen atom, chlorine atom and methyl group.

$R^6$ is preferably methyl, ethyl, propyl, butyl, pentyl and allyl groups; methoxymethyl, ethoxymethyl, propoxymethyl, 2-methoxyethyl, 2-ethoxyethyl, 2-propoxyethyl, 2-allyloxyethyl, 2-propargyloxyethyl and 2-benzyloxyethyl groups.

$A^1$ is preferably ethylene or 1-methylethylene group. $A^2$ is preferably methylene or ethylene group.

X is preferably oxygen atom.

In the above formula (I), when either one of the carbon atoms is asymmetric carbon, individual optical isomers and racemic compounds or mixtures thereof are all included in the present invention.

The compound (I) of the present invention can be easily prepared according to, for example, the method shown below.

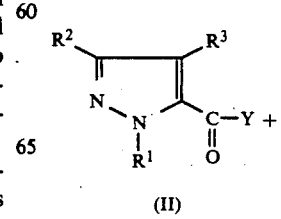

(II)

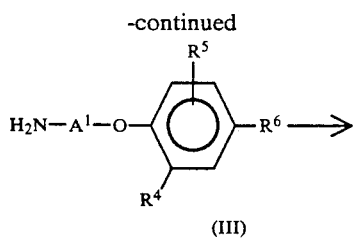

(III)

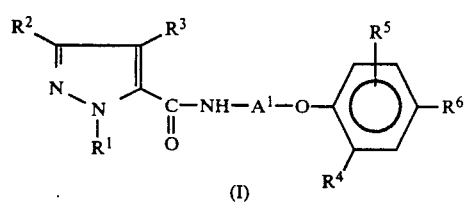

(I)

wherein $A^1$, $R^1$, $R^2$, $R^3$, $R^4$, $R^5$ and $R^6$ are the same as defined above, and Y represents a halogen atom.

As the halogen atom, chlorine and bromine may be included.

As is apparent from the above reaction scheme, in the present reaction, the compound H—Y is eliminated, and for permitting the reaction to proceed smoothly by capturing this, it is preferable to carry out the reaction in the presence of a base.

The reaction is generally carried out in the presence of a solvent, but it is possible to carry out the reaction between the compounds of the formula (II) and the formula (III) without a solvent.

The solvent is not particularly limited, provided that it does not interfere with the present reaction, including aromatic, aliphatic, alicyclic hydrocarbons which are chlorinated or not, such as benzene, toluene, xylene, methylnaphthalene, petroleum ether, ligroin, hexane, chlorobenzene, dichlorobenzene, methylene chloride, chloroform, dichloroethane, trichloroethylene, cyclohexane; ethers such as diethyl ether, ethylene glycol dimethyl ether, tetrahydrofuran, dioxane; ketones such as acetone, methyl ethyl ketone, methyl isobutyl ketone; and mixtures of the solvents as mentioned above.

As the base, there may be included organic bases such as triethylamine, pyridine, N,N-dimethylaniline; alkali metal alkoxides such as sodium methoxide, sodium ethoxide; inorganic bases such as sodium hydride, sodium amide, sodium hydroxide, potassium hydroxide, sodium carbonate, potassium carbonate.

The reaction temperature may be generally an ice-cooling temperature or higher to not higher than the boiling point of the solvent used, preferably 0° C. to 10° C.

The starting material (II) to be used in the present reaction can be prepared according to the method described in Bull. Soc. Chim. France, 293 (1966), and the starting material (III) can be easily prepared, for example, according to the method known per se as shown below.

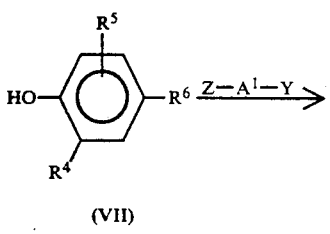

(VII)

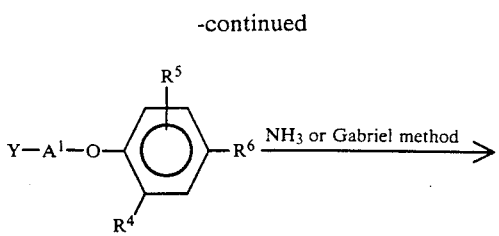

(V)

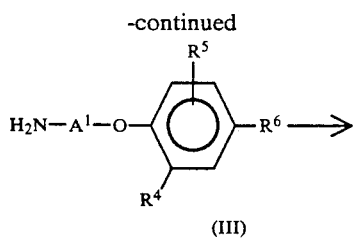

(III)

wherein $R^4$, $R^5$, $R^6$ and Y are the same as defined above, and Z represents an eliminatable group.

As the eliminatable group, halogen atoms such as chlorine, bromine, etc., or alkanesulfonic acid residues, arylsulfonic acid residues, etc. may be included.

The desired product (I) obtained according to the method as described above can be suitably purified by known means such as recrystallization, various chromatographies, etc.

The insecticide, acaricide and fungicide of the present invention contain one kind or several kinds of the compounds of the formula (I) as the active ingredient. Although the compound of the formula (I) itself may be also used, it is generally prepared in a conventional manner by formulation with common carriers, surfactants, dispersing agents or auxiliary agents, etc. into a composition such as powder, wettable agent, emulsion, fine granule, granule, aqueous or oily suspension, aerosol, etc.

Suitable carriers may include, for example, solid carriers such as talc, bentonite, clay, kaolin, diatomaceous earth, white carbon, vermiculite, slaked lime, siliceous sand, ammonium sulfate and urea; liquid carriers, including hydrocarbons such as kerosine and mineral oil; aromatic hydrocarbons such as benzene, toluene and xylene; chlorinated hydrocarbons such as chloroform and carbon tetrachloride; ethers such as dioxane and tetrahydrofuran; ketones such as acetone, cyclohexanone and isophorone; esters such as ethyl acetate, ethylene glycol acetate and dibutyl maleate; alcohols such as methanol, n-hexanol and ethylene glycol; polar solvents such as dimethylformamide and dimethyl sulfoxide; or water. Also, as the gaseous carrier, air, carbon dioxide gas and Freon can be used and mixed with the compound to be jetted.

As the surfactant for improvement of attachment, absorption of the present agent onto animals and plants, improvement of performances such as dispersion, emulsification and spreading of the chemical, for example, alcohol sulfates, alkylsulfonic acid salts, ligninsulfonic acid salts and polyoxyethylene glycols may be employed.

Further, for improvement of the properties of the preparation, as the auxiliary agent, for example, carboxymethyl cellulose, polyethylene glycol and gum arabic may be employed.

The above-mentioned carrier, surfactant, dispersing agent and auxiliary agent may be employed individually or in combination depending on the respective purposes.

The active ingredient concentration when the compound of the present invention is formed into a preparation may be generally 1 to 50 % by weight in the case of emulsion, generally 0.3 to 25 % by weight in the case of powder, generally 1 to 90 % by weight in the case of a wettable agent, generally 0.5 to 5 % by weight in the case of a granule, generally 0.5 to 5 % by weight in the case of an oil, generally 0.5 to 5 % by weight in the case of an aerosol, preferably the preparation comprises 10 % of the compound of the present invention and 90 % of a carrier.

These preparations are diluted to an appropriate concentration and sprayed onto plant stalks and leaves, soil or the water surface of a paddy field, or alternatively directly applied. Thus, depending on the respective purposes, they can be provided for various uses.

The compounds of the present invention exhibit excellent effects against agricultural and horticultural injurious insects, including Hemiptera such as planthoppers, leafhoppers, aphids and whiteflies; Lepidoptera such as diamondback moth, leaf roller worms, pyralid moths and common cabbage worm; Coleoptera such as weevils and leaf beetles; and otherwise Acarina such as citrus red mite and twospotted spider mite.

Also, they are effective for control of hygienically injurious insects such as flies, mosquitos, cockroaches, etc. and otherwise also effective against injurious insects to stored grains, etc.

Further, the compounds of the present invention have also activities against root-knot nematode, pine wood nematode, bulb mite in the soil.

Also, the compounds of the present invention are effective for prevention and curing of injurious diseases for agriculture and horticulture, and extremely effective for, for example, rice blast, barley powdery mildew, cucumber downy mildew, cucumber gray mold and tomato diseases.

Thus, the compounds of the present invention have extremely wide uses and application fields, having also high activities, and can be provided for practical application in various preparation forms.

EXAMPLES

In the following, the present invention will be described in more detail by referring to Examples, but the scope of the present invention is not limited to these Examples at all.

EXAMPLE 1

Preparation of
N-{2-4-(2-ethoxyethyl)-2-methylphenoxyl}-ethyl}-4-chloro-1,3-dimethyl-5-pyrazolecarboxamide A solution of 1.2 g of 2-[4-(2-ethoxyethyl)-2-methylphenoxy]ethylamine and 1 ml of triethylamine dissolved in 30 ml of toluene was stirred under ice-cooling. To the solution was added dropwise 20 ml of 1.0 g of 4-chloro-1,3-dimethyl-5-pyrazolecarboxylic acid chloride in toluene at 0° to 10° C., and the mixture was stirred for 2 hours after the dropwise addition.

After completion of the reaction, the precipitated triethylamine hydrochloride was separated by filtration, the filtrate was concentrated under reduced pressure, the triethylamine hydrochloride obtained was separated by filtration, the filtrate was concentrated under reduced pressure, and the oily product obtained was isolated by column chromatography (Wako Gel C-200, eluted with ethyl acetate : toluene = 1:3) to give 1.5 g of the title product as colorless crystals. m.p. 52° to 54° C.

EXAMPLE 2

Preparation of
N-{2-[4-(2-ethoxyethyl)-2,6-dimethylphenoxylethyl}-4-bromo-1,3-dimethyl-5-pyrazolecarboxamide A solution of 1.2 g of 2-[4-(2-ethoxyethyl)-2,6-dimethylphenoxy]ethylamine and 1 ml of triethylamine dissolved in 30 ml of toluene was stirred under ice-cooling. To the solution was added dropwise 20 ml of a solution of 1.2 g of 4-bromo-1,3-dimethyl-5-pyrazolecarboxylic acid chloride in toluene at 0° to 10° C., and the mixture was stirred for 2 hours after the dropwise addition.

After completion of the reaction, the precipitated triethylamine hydrochloride was separated by filtration, the filtrate was concentrated under reduced pressure, and the oily product obtained was isolated by column chromatography (Wako Gel C-200, eluted with ethyl acetate : toluene =1:3) to give 1.7 g of the title product as colorless crystals. m.p. 112° to 114° C.

According to the method in Examples 1, 2, the compounds shown in Table 1 were obtained.

TABLE 1

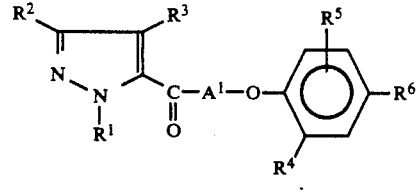

| Compound No. | $A^1$ | $R^1$ | $R^2$ | $R^3$ | $R^4$ | $R^5$ | $R^6$ | Physical property |
|---|---|---|---|---|---|---|---|---|
| 1 | —CH₂CH₂— | CH₃ | CH₃ | Cl | H | H | H | m.p. 54~56° |
| 2 | " | " | " | " | CH₃ | " | " | m.p. 68~71° |
| 3 | " | " | " | " | " | " | CH₃ | m.p. 87~90° |
| 4 | " | " | " | " | " | " | n-C₅H₁₁ | $n_D^{25.1}$ 1.5380 |
| 5 | " | " | " | " | Br | " | —CH₂CH=CH₂ | m.p. 60~63° |
| 6 | " | " | " | " | Cl | " | —CH₂CH₂OCH₃ | m.p. 62~65° |
| 7 | " | " | " | " | " | " | —CH₂CH₂OC₂H₅ | m.p. 52~54° |
| 8 | —CH₂CH₂— | CH₃ | CH₃ | Cl | H | H | —CH₂CH₂OC₃H₇ | m.p. 54~56° |
| 9 | " | " | " | " | " | " | —CH₂CH₂OCH₂CH=CH₂ | m.p. 55~57° |

TABLE 1-continued

| Compound No. | $A^1$ | $R^1$ | $R^2$ | $R^3$ | $R^4$ | $R^5$ | $R^6$ | Physical property |
|---|---|---|---|---|---|---|---|---|
| 10 | " | " | " | " | " | " | $-CH_2CH_2OCH_2C\equiv CH$ | m.p. 62~64° |
| 11 | " | " | " | " | " | " | $-CH_2CH_2OCH_2-\bigcirc$ | |
| 12 | " | " | t-$C_4H_9$ | " | " | " | $CH_3$ | $n_D^{22.1}$ 1.5438 |
| 13 | " | " | " | " | " | " | n-$C_5H_{11}$ | $n_D^{22.1}$ 1.5325 |
| 14 | " | " | " | " | " | " | $-CH_2CH_2OCH_3$ | $n_D^{22.6}$ 1.5362 |
| 15 | " | " | " | " | " | " | $-CH_2CH_2OC_2H_5$ | $n_D^{22.1}$ 1.5347 |
| 16 | " | " | $CH_3$ | Br | " | 6-$CH_3$ | " | m.p. 112~114° |
| 17 | " | " | " | " | " | H | $-CH_2CH_2OC_2H_5$ | $n_D^{26.0}$ 1.5445 |
| 18 | " | " | " | H | " | 6-Cl | n-$C_4H_9$ | $n_D^{22.1}$ 1.5415 |
| 19 | $-CH_2CH_2-$ | $CH_3$ | $CH_3$ | H | $CH_3$ | H | $-CH_2CH_2OC_2H_5$ | m.p. 47~50° |
| 20 | " | " | " | $CH_3$ | " | " | " | |
| 21 | " | H | " | Cl | " | " | " | m.p. 91~93° |
| 22 | " | " | " | " | " | " | n-$C_5H_{11}$ | m.p. 111~113° |
| 23 | " | $CH_3$ | " | " | H | " | $-CH_2CH_2OCH_3$ | |
| 24 | " | " | " | " | " | " | $-CH_2OC_2H_5$ | |
| 25 | " | " | " | " | " | " | $-CH_2OC_3H_7$ | |
| 26 | " | " | " | H | $CH_3$ | 3-$CH_3$ | $-CH_2CH_2OC_2H_5$ | m.p. 104~106° |
| 27 | " | " | " | " | " | H | $-CH_2C=CH_2$<br>$\|$<br>$CH_3$ | $n_D^{22.1}$ 1.5484 |
| 28 | $-CH-CH_2-$<br>$\|$<br>$CH_3$ | " | " | " | " | " | n-$C_5H_{11}$ | $n_D^{22.2}$ 1.5316 |
| 29 | $-CH_2-CH-$<br>$\|$<br>$C_2H_5$ | " | " | " | " | 6-$CH_3$ | $CH_3$ | $n_D^{22.2}$ 1.5411 |
| 30 | $-CH_2CH_2-$ | $CH_3$ | $C_2H_5$ | Cl | $CH_3$ | H | $-CH_2CH_2OC_2H_5$ | m.p. 36~38° |
| 31 | " | " | " | Br | " | " | $-CH_2CH_2OCH_3$ | m.p. 47~49° |
| 32 | " | " | n-$C_3H_7$ | Cl | " | " | " | |
| 33 | " | " | " | Br | " | " | " | |
| 34 | " | " | $C_2H_5$ | Cl | " | " | n-$C_5H_{11}$ | $n_D^{27.4}$ 1.5326 |
| 35 | " | " | " | " | " | 6-Cl | n-$C_4H_9$ | m.p. 55~58° |
| 36 | " | " | " | " | " | H | $-CH_2CH_2OCH_2C\equiv CH$ | m.p. 66~67° |
| 37 | " | " | " | " | " | 6-$CH_3$ | $-CH_2CH_2OC_2H_5$ | m.p. 75~77° |
| 38 | $-CH-CH_2-$<br>$\|$<br>$CH_3$ | " | " | " | " | H | n-$C_5H_{11}$ | $n_D^{27.4}$ 1.5275 |
| 39 | $-CH_2CH_2-$ | " | " | Br | " | " | " | $n_D^{27.6}$ 1.5368 |
| 40 | " | " | " | " | " | H | $-CH_2OC_2H_5$ | $n_D^{27.6}$ 1.5503 |

Of these compounds in Table 1, particularly preferred compounds in the present invention are as follows:

N-{2-[4-(2-methoxyethyl)-2-methylphenoxy]-ethyl}-4-chloro-1,3-dimethyl-5-pyrazolecarboxamide (Compound No. 6)

N-{2-[4-(2-ethoxyethyl)-2-methylphenoxy]-ethyl}-4-chloro-1,3-dimethyl-5-pyrazolecarboxamide (Compound No. 7)

N-{2-[4-(2-n-propoxyethyl)-2-methylphenoxy]-ethyl}-4-chloro-1,3-dimethyl-5-pyrazolecarboxamide (Compound No. 8)

N-(2-[4-(2-allyloxyethyl)-2-methylphenoxy]-ethyl)-4-chloro-1,3-dimethyl-5-pyrazolecarboxamide (Compound No. 9)

N-(2-[4-(2-propargyloxyethyl)-2-methylphenoxy]-ethyl)-4-chloro-1,3-dimethyl-5-pyrazolecarboxamide (Compound No. 10)

N-{2-[4-(2-ethoxyethyl)-2,6-dimethylphenoxy]-ethyl)-4-bromo-1,3-dimethyl-5-pyrazolecarboxamide (Compound No. 16)

N-(2-[4-(2-ethoxyethyl)-2-methylphenoxy]-ethyl}-4-bromo-1,3-dimethyl-5-pyrazolecarboxamide (Compound No. 17)

N-(2-[4-(2-ethoxyethyl)-2-methylphenoxy]-ethyl}-4-chloro-1-methyl-3-ethyl-5-pyrazolecarboxamide (Compound No. 30)

N-(2-[4-(2-methoxyethyl)-2-methylphenoxy]-ethyl)-4-bromo-1-methyl-3-ethyl-5-pyrazolecarboxamide (Compound No. 31)

N-{2-[4-(2-propargyloxyethyl)-2-methylphenoxy]-ethyl}-4-chloro-1-methyl-3-ethyl-5-pyrazolecarboxamide (Compound No. 36)

N-{2-[4-(2-ethoxyethyl)-2,6-dimethylphenoxy]-ethyl}-4-chloro-1-methyl-3-ethyl-5-pyrazolecarboxamide (Compound No. 37) and N-[2-(4-ethoxymethylphenoxy)-ethyl]-4-bromo-1-methyl-3-ethyl-5-pyrazolecarboxamide (Compound No. 40)

EXAMPLE 3

Five parts by weight of the compound of Compound No. 4, 35 parts by weight of bentonite, 57 parts by weight of talc, 1 part by weight of Neopelex powder (trade name: manufactured by Kao-Atlas) and 2 parts by weight of sodium lignin sulfonate were homogeneously mixed, and then kneaded with addition of a small amount of water, followed by granulation and drying to obtain granules.

EXAMPLE 4

Ten parts by weight of the compound of Compound No. 7, 70 parts by weight of kaolin, 18 parts by weight of white carbon, 1.5 parts by weight of Neopelex powder (trade name: manufactured by Kao-Atlas) and 0.5 part by weight of Demol (trade name: manufactured by Kao-Atlas) were homogeneously mixed, and then pulverized to obtain a wettable agent.

EXAMPLE 5

To 20 parts by weight of the compound of Compound No. 16 and 70 parts by weight of xylene were added 10 parts by weight of Toxanone (trade name: manufactured by Sanyo Kasei Kogyo), and the mixture was homogeneously mixed and dissolved to obtain an emulsion.

EXAMPLE 6

Five parts by weight of the compound of Compound No. 28, 50 parts by weight of talc and 45 parts by weight of kaolin were homogeneously mixed to obtain powder.

EXAMPLE 7

Activity test against green rice leafhopper

The compounds shown in Table 1 were formulated similarly as described in Example 4, and each wettable agent prepared was diluted to 300 ppm with water containing a surfactant (0.01%) to prepare a chemical solution. In each chemical solution was dipped young rice seedlings for 30 seconds, and the rice seedlings after air drying were inserted into a glass cylinder. Ten 4th instar green rice leafhopper nymphs were freed into the cylinder, and the cylinder was left to stand stoppered with a porous plug in a thermostatic chamber of 25° C. Four days later, the number of live and dead nymphs were counted to determine the insecticide ratio. The results are shown in Table 2.

Those with insecticide ratio of 100 % are shown as A, those with 99 to 80 % as B, those with 79 to 60 % as C and those with less than 60 % as D.

TABLE 2

| Green rice leafhopper | |
| --- | --- |
| Compound No. | Effect |
| 4 | A |
| 5 | A |
| 6 | A |
| 7 | A |
| 8 | A |
| 9 | A |
| 10 | A |
| 16 | A |
| 17 | A |
| 30 | A |
| 31 | A |
| 35 | B |
| 37 | A |

EXAMPLE 8

Activity test against female adult of twospotted spider mite

The compounds shown in Table 1 were formed into preparations similarly as in Example 4, and each preparation was diluted to 300 ppm with water containing a surfactant (0.01%), and in each chemical solution was dipped kidney bean leaf disk (diameter 20 mm) on which 10 female adults of twospotted spider mites had been infested for 10 seconds. The leaf disk was left to stand in a thermostatic chamber of 25° C., and 3 days later the numbers of live and dead mites were counted to determine the acaricide ratio, and the results are shown in Table 3.

The acaricide ratio is represented by the same standards as the insecticide ratio in Example 7.

TABLE 3

| Adult twospotted spider mite | |
| --- | --- |
| Compound No. | Effect |
| 4 | A |
| 6 | A |
| 7 | A |
| 8 | A |
| 9 | A |
| 10 | A |
| 17 | A |
| 30 | A |
| 31 | A |
| 34 | A |
| 35 | B |
| 36 | B |
| 37 | A |
| 38 | A |
| 39 | A |
| 40 | B |

EXAMPLE 9

Activity test against egg of twospotted spider mite

Five female adults of twospotted spider mites were infested on kidney bean leaf disk (diameter 20 mm), then the adult mites were removed and the number of eggs produced was counted. On the other hand, the compounds shown in Table 1 were prepared similarly as in Example 4 and diluted to 300 ppm with water containing a surfactant (0.01%). In each chemical solution was dipped the leaf disk for 10 seconds. The leaf disk was left to stand in a thermostatic chamber of 25° C., and 6 days later the number of unhatched eggs was counted to determine the killing ratio of egg to obtain the results shown in Table 4. The killing ratio of egg is represented by the same standards as the insecticide ratio in Example 7.

TABLE 4

| Egg of twospotted spider mite | |
|---|---|
| Compound No. | Effect |
| 2 | A |
| 4 | A |
| 5 | A |
| 6 | A |
| 7 | A |
| 8 | A |
| 9 | A |
| 10 | A |
| 16 | A |
| 17 | A |
| 18 | A |
| 19 | A |
| 27 | A |
| 30 | A |
| 31 | A |
| 34 | A |
| 35 | A |
| 36 | A |
| 37 | A |
| 38 | A |
| 39 | A |
| 40 | B |

EXAMPLE 10

Control activity test against cucumber gray mold (Prevention effect)

In plastic planting pots of 6 cm in diameter, one cucumber (species: Sagami Hanshiro) was grown per pot, and onto young plant body with leaf being firstly developed was sprayed 20 ml per pot of a wettable agent prepared similarly as in Example 4 and diluted to 500 ppm with water containing a surfactant (0.01%).

After spraying, the plant was cultivated in a glass greenhouse for 2 days, and then a suspension of cucumber gray mold conidial spores ($5 \times 10^3$ spores/ml) was uniformly inoculated by spraying.

After inoculation, the plant was grown in the inoculation chamber for 2 days, and the extent of cucumber gray mold lesions appeared on leaflets was examined. The effect of the chemical was judged as compared with the extent of lesions in the non-treated leaf.

Evaluation is shown by the 6 ranks of 5 to 0, and one without lesion is shown by 5, one with 10 % or less lesion area as compared with non-treated district by 4, one with about 20% by 3, one with about 40 % by 2, one with about 60 % by 1, and one wholly afflicted by 0. The results are shown in Table 5.

TABLE 5

| Compound No. | Effect |
|---|---|
| 4 | 3 |
| 6 | 4 |
| 8 | 5 |
| 17 | 3 |
| Non-treated | 0 |

EXAMPLE 11

Control activity test against cucumber downy mildew (Prevention effect)

In plastic planting pots of 6 cm in diameter, one cucumber (species: Sagami Hanshiro) was grown per pot, and onto young plant body of 1.5-leaf stage was sprayed 20 ml per pot of a wettable agent prepared similarly as in Example 4 and diluted to 500 ppm with water containing a surfactant (0.01%).

After spraying, the plant was cultivated in a glass greenhouse for 2 days, and then a suspension of cucumber downy mildew zoospores was prepared from afflicted leaves and uniformly inoculated by spraying on the under surface of the primary leaf.

After inoculation, after maintained under darkness at 20° C. for 2 days, the plant was grown in a glass greenhouse for 5 days, and the extent of cucumber downy mildew lesions appeared on the first leaf was examined. The effect of the chemical was judged as compared with the extent of lesions in the non-treated leaf, and the results are shown in Table 6.

Evaluation is represented by the same standards as in Example 10.

TABLE 6

| Compound No. | Effect |
|---|---|
| 26 | 5 |
| Non-treated | 0 |

EXAMPLE 12

Control activity test against wheat rust (Prevention effect)

In plastic planting pots of 6 cm in diameter, ten wheats (species: Kobushikomugi) were grown per pot, and onto young plant body of 1.5-leaf stage was sprayed 20 ml per pot of a wettable agent prepared similarly as in Example 4 and diluted to 500 ppm with water containing a surfactant (0.01%).

After spraying, the plant was cultivated in a glass greenhouse for 2 days, and then a suspension of wheat red rust spores ($7 \times 10^4$ spores/ml) was uniformly inoculated by spraying.

After inoculation, the plant was grown in a glass greenhouse for one week, and the extent of wheat red rust lesions appeared on the first leaf was examined. The effect of the chemical was judged as compared with the extent of lesions in the non-treated leaf to obtain the results shown in Table 7.

Evaluation is represented by the same standards as in Example 10.

TABLE 7

| Compound No. | Effect |
|---|---|
| 2 | 5 |
| 3 | 3 |
| 4 | 4 |
| 6 | 5 |
| 8 | 5 |
| 9 | 5 |
| 10 | 5 |
| 17 | 4 |
| 18 | 4 |
| 19 | 5 |
| 27 | 3 |
| 28 | 4 |
| 29 | 4 |
| 30 | 4 |
| 31 | 5 |
| 34 | 5 |
| 35 | 5 |
| 36 | 5 |
| 37 | 5 |
| 38 | 5 |
| 39 | 5 |
| 40 | 5 |
| Non-treated | 0 |

EXAMPLE 13

Control activity test against barley powdery mildew (Prevention effect)

In plastic planting pots of 6 cm in diameter, ten barleys (species: Kuromugi) were grown per pot, and onto young plant body of 1.5-leaf stage was sprayed 20 ml per pot of a wettable agent prepared similarly as in Example 4 and diluted to 500 ppm with water containing a surfactant (0.01%).

After spraying, the plant was cultivated in a glass greenhouse for 2 days, and then barley powdery mildew conidia were collected from the afflicted leaves and uniformly inoculated by spraying from above the plant body.

After inoculation, the plant was grown in a glass greenhouse for one week, and the extent of barley powdery mildew lesions appeared on the first leaf was examined. The effect of the chemical was judged as compared with the extent of lesions in the non-treated leaf to obtain the results shown in Table 8.

Evaluation is represented by the same standards as in Example 10.

TABLE 8

| Compound No. | Effect |
| --- | --- |
| 3 | 5 |
| 5 | 4 |
| 6 | 5 |
| 8 | 4 |
| 9 | 4 |
| 10 | 4 |
| 28 | 5 |
| 31 | 5 |
| 35 | 3 |
| 36 | 4 |
| 37 | 4 |
| Non-treated | 0 |

EXAMPLE 14

Control activity test against rice blast (Prevention effect)

In plastic planting pots of 6 cm in diameter, ten rice (species: Nipponbare) were grown per pot, and onto young plant body of 1.5-leaf stage was sprayed 20 ml per pot of a wettable agent prepared similarly as in Example 4 and diluted to 500 ppm with water containing a surfactant (0.01%).

After spraying, the plant was cultivated in a glass greenhouse for 2 days, and then rice blast conidia were collected from the afflicted leaves and uniformly inoculated by spraying onto the plant leaves.

After inoculation, the plant was grown in a greenhouse of 28° C. for 5 days, and the extent of rice blast lesions appeared on the leaf was examined. The effect of the chemical was judged as compared with the extent of lesions in the non-treated leaf to obtain the results shown in Table 9.

Evaluation is represented by the same standards as in Example 10.

TABLE 9

| Compound No. | Effect |
| --- | --- |
| 30 | 4 |
| 31 | 3 |
| 34 | 3 |
| 36 | 3 |
| 40 | 5 |

TABLE 9-continued

| Compound No. | Effect |
| --- | --- |
| Non-treated | 0 |

We claim:

1. A phenoxyalkylamine compound of a formula (I):

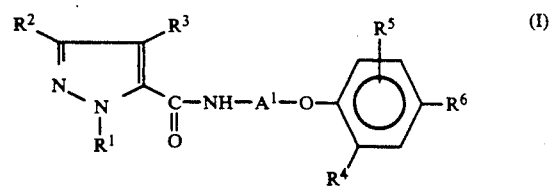

wherein $A^1$ represents an alkylene group having 2 to 5 carbon atoms, $R^1$ and $R^2$ each represent a hydrogen atom or a lower alkyl group having 1 to 5 carbon atoms, $R^3$, $R^4$ and $R^5$ each represent a hydrogen atom, a lower alkyl group having 1 to 5 carbon atoms or a halogen atom, $R^6$ represents a hydrogen atom, a lower alkyl group having 1 to 5 carbon atoms, an alkenyl group having 3 to 5 carbon atoms or a group $—A^2—X—R^7$, $A^2$ represents an alkylene group having 1 to 5 carbon atoms, X represents an oxygen atom or a sulfur atom, $R^7$ represents a lower alkyl group having 1 to 5 carbon atoms, an alkenyl group having 3 to 5 carbon atoms or a substituted or unsubstituted aralkyl group.

2. The phenoxyalkylamine compound according to claim 1, wherein $R^1$ and $R^2$ are a lower alkyl group which is a straight or branched alkyl group selected from the group consisting of a methyl group, an ethyl group, a propyl group, an isopropyl group, a butyl group, an isobutyl group, a sec-butyl group, a t-butyl group, an amyl group, an isoamyl group and a sec-amyl group.

3. The phenoxyalkylamine compound according to claim 1, wherein $R^3$ is a halogen atom is selected from the group consisting of fluorine, chlorine, bromine and iodine.

4. The phenoxyalkylamine compound according to claim 1, wherein $R^6$ is a straight or branched alkenyl group selected from the group consisting of an allyl group, a 1-butenyl group, 2-butenyl group, a 1-methylallyl group, a 2-methylallyl group, a 2-pentenyl group and an isoprenyl group.

5. The phenoxyalkylamine compound according to claim 1, wherein $R^7$ is a substituted or unsubstituted aralkyl group selected from the group consisting of a benzyl group, a 1-phenethyl group, a 2-phenethyl group, a 4-chlorobenzyl group, a 4-fluorobenzyl group, a 4-methylbenzyl group, a 3,4-dichlorobenzyl group and a 2,4-difluorobenzyl group.

6. The phenoxyalkylamine compound according to claim 1, wherein the alkylene group represented by $A^1$ is a straight or branched alkylene group selected from the group consisting of an ethylene group, a trimethylene group, a 1-methylethylene group, a 2-methylethylene group, a tetramethylene group, 1-ethylethylene group, a 2-ethylethylene group, a dimethylmethylene group and a pentamethylene group.

7. The phenoxyalkylamine compound according to claim 1, wherein $R^1$ is a methyl group, $R^2$ is a methyl group, an ethyl group or a propyl group, $R^3$ is a chlorine atom or a bromine atom, R⁴ and R⁵ are any one of a hydrogen atom, a chlorine atom and a methyl group.

8. The phenoxyalkylamine compound according to claim 1, wherein R⁶ is selected from the group consisting of a methyl group, an ethyl group, a propyl group, a butyl group, a pentyl group, an allyl group, a methoxymethyl group, an ethoxymethyl group, a propoxymethyl group, a 2-methoxyethy group, a 2-ethoxyethyl group, a 2-propoxyethyl group, a 2-allyloxyethyl group, a 2-propargyloxyethyl group and a 2-benzyloxyethyl group.

9. The phenoxyalkylamine compound according to claim 8, wherein A¹ is an ethylene group or a 1-methylethylene group and A² is a methylene group or an ethylene group.

10. The phenoxyalkylamine compound according to claim 9, wherein X is an oxygen atom.

11. The phenoxyalkylamine compound according to claim 1, wherein the compound is N-(2-(4-n-pentyl-2-methylphenoxy)ethyl)-4-chloro-1,3-dimethyl-5-pyrazolecarboxamide.

12. The phenoxyalkylamine compound according to claim 1, wherein the compound is N-(2-(4-allyl-2-methylphenoxy)ethyl)-4-bromo-1,3-dimethyl-5-pyrazolecarboxamide.

13. The phenoxyalkylamine compound according to claim 1, wherein said compound is N-{2-(4-(2-methoxyethyl)-2-methylphenol methoxyphenoxy)-ethyl}-4-chloro-1,3-dimethyl-5-pyrazolecarboxamide.

14. The phenoxyalkylamine compound according to claim 1, wherein said compound is N-{2-(4-(2-ethoxyethyl)-2-methylphenoxy)-ethyl}-4-chloro-1,3-dimethyl-5-pyrazolecarboxamide.

15. The phenoxyalkylamine compound according to claim 1, wherein said compound is N-{2-(4-(2-n-propoxyethyl)-2-methylphenoxy)-ethyl}-4-chloro-1,3-dimethyl-5-pyrazolecarboxamide.

16. The phenoxyalkylamine compound according to claim 1, wherein said compound is N-{2-(4-(2-allyloxyethyl)-2-methylphenoxy)-ethyl)-4-chloro-1,3-dimethyl-5-pyrazolecarboxamide.

17. The phenoxyalkylamine compound according to claim 1, wherein said compound is N-{2-(4-(2-propargyloxyethyl)-2-methylphenoxy)-ethyl}-4-chloro-1,3-dimethyl-5-pyrazolecarboxamide.

18. The phenoxyalkylamine compound according to claim 1, wherein said compound is N-{2-(4-(2-ethoxyethyl)-2,6-dimethylphenoxy)-ethyl}-4-bromo-1,3-dimethyl-5-pyrazolecarboxamide.

19. The phenoxyalkylamine compound according to claim 1, wherein said compound is N-{2-(4-(2-ethoxyethyl)-2-methylphenoxy)-ethyl}-4-bromo-1,3-dimethyl-5-pyrazolecarboxamide.

20. The phenoxyalkylamine compound according to claim 1, wherein said compound is N-{2-(4-(2-ethoxyethyl)-2-methylphenoxy)-ethyl}-4-chloro-1-methyl-3-ethyl-5-pyrazolecarboxamide.

21. The phenoxyalkylamine compound according to claim 1, wherein said compound is N-{2-(4-(2-methoxyethyl)-2-methylphenoxy)-ethyl}-4-bromo-1-methyl-3-ethyl-5-pyrazolecarboxamide.

22. The phenoxyalkylamine compound according to claim 1, wherein said compound is N-{2-(4-(2-propargyloxyethyl)-2-methylphenoxy)-ethyl}-4-chloro-1-methyl-3-ethyl-5-pyrazolecarboxamide.

23. The phenoxyalkylamine compound according to claim 1, wherein said compound is N-{2-(4-(2-ethoxyethyl)-2,6-dimethylphenoxy)-ethyl}-4-chloro-1-methyl-3-ethyl-5-pyrazolecarboxamide.

24. The phenoxyalkylamine compound according to claim 1, wherein said compound is N-(2-(4-ethyoxymethylphenoxy)-ethyl)-4-bromo-1-methyl-3-ethyl-5-pyrazolecarboxamide.

25. The phenoxyalkylamine compound according to claim 1, wherein R¹ is a lower alkyl group having 1 to 5 carbon atoms.

26. An insecticide and an acaricide composition for agriculture and horticulture, comprising a carrier and an insecticidal and acaricidal amount of a phenoxyalkylamine formula (I) as an active ingredient:

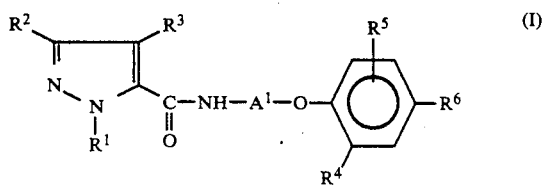

wherein A¹ represents an alkylene group having 2 to 5 carbon atoms, R¹ and R² each represent a hydrogen atom or a lower alkyl group having 1 to 5 carbon atoms, R³, R⁴ and R⁵ each represent a hydrogen atom, a lower alkyl group having 1 to 5 carbon atoms, or a halogen atom, R⁶ represents a hydrogen atom, a lower alkyl group having 1 to 5 carbon atoms, an alkenyl group having 3 to 5 carbon atoms, or a group —A²—X—R⁷, A² represents an alkylene group having 1 to 5 carbon atoms, X represents an oxygen atom or a sulfur atom, R⁷ represents a lower alkyl group having 1 to 5 carbon atoms, an alkenyl group having 3 to 5 carbon atoms, an alkynyl group having 3 to 5 carbon atoms or a substituted or unsubstituted aralkyl group.

27. The insecticide and arcaricide composition for agriculture and horticulture according to claim 12, which comprises about 10% of the compound of the formula (I) and about 90% of a carrier.

28. The composition according to claim 27, wherein the compound is at least one compound selected from the group consisting of
N-{2-(4-(2-methoxyethyl)-2-methylphenoxy)-ethyl}-4-chloro-1,3-dimethyl-5-pyrazolecarboxamide,
N-{2-(4-(2-ethoxyethyl)-2-methylphenoxy)-ethyl}-4-chloro-1,3-dimethyl-5-pyrazolecarboxamide,
N-{2-(4-(2-n-propoxyethyl)-2-methylphenoxy)-ethyl}-4-chloro-1,3-dimethyl-5-pyrazolecarboxamide,
N-{2-(4-(2-allyloxyethyl)-2-methylphenoxy)-ethyl}-4-chloro-1,3-dimethyl-5-pyrazolecarboxamide,
N-{2-(4-(2-propargyloxyethyl)-2-methylphenoxy)-ethyl}-4-chloro-1,3-dimethyl-5-pyrazolecarboxamide,
N-{2-(4-(2-ethoxyethyl)-2,6-dimthylphenoxy)-ethyl}-4-bromo-1,3-dimethyl-5-pyrazolecarboxamide,
N-{2-(4-(2-ethoxyethyl)-2-methylphenoxy)-ethyl}-4-bromo-1,3-dimethyl-5-pyrazolecarboxamide,
N-{2-(4-(2-ethoxyethyl)-2-methylphenoxy)-ethyl}-4-chloro-1-methyl-3-ethyl-5-pyrazolecarboxamide,
N-{2-(4-(2-methoxyethyl)-2-methylphenoxy)-ethyl}-4-bromo-1-methyl-3-ethyl-5-pyrazolecarboxamide,
N-{2-(4-(2-propargyloxyethyl)-2-methylphenoxy)-ethyl}-4-chloro-1-methyl-3-ethyl-5-pyrazolecarboxamide, N-{2-(4-(2-ethoxyethyl)-2,6-dimethylphenoxy)-ethyl}-4-chloro-1-methyl-3-ethyl-5-pyrazolecarboxamide and N-{2-(4-ethoxymethylphenoxy)-ethyl-4-bromo-1-methyl-3-ethyl-5-pyrazolecarboxamide.

29. The composition according to claim 27, wherein the compound is selected from the group consisting of N-(2-(4-n-pentyl-2-methylphenoxy)ethyl)-4-chloro-1,3-dimethyl-5-pyrazolecarboxamide and N-(2-(4-allyl-2-methylphenoxy)ethyl)-4-bromo-1,3-dimethyl-5-pyrazolecarboxamide.

30. A method for combatting insects and acarids comprising applying to insects and acarids or a locus thereof an effective insecticidal and acaricidal amount of a phenoxylalkylamine compound of a formula (I)

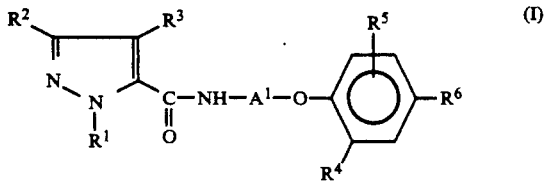

wherein $A^1$ represents an alkylene group having 2 to 5 carbon atoms, $R^1$ and $R^2$ each represent a hydrogen atom or a lower alkyl group having 1 to 5 carbons atoms, $R^3$, $R^4$ and $R^5$ each represent a hydrogen atom, a lower alkyl group having 1 to 5 carbon atoms or a halogen atom, $R^6$ represents a hydrogen atom, a lower alkyl group having 1 to 5 carbon atoms, an alkenyl group having 3 to 5 carbon atoms or a group —$A^2$—X—$R^7$, $A^2$ represents an alkylene group having 1 to 5 carbon atoms, X represents an oxygen atom or a sulfur atom, $R^7$ represents a lower alkyl group having 1 to 5 carbon atoms, an alkenyl group having 3 to 5 carbon atoms, an alkynyl group having 3 to 5 carbon atoms or a substituted or unsubstituted aralkyl group.

31. The method according to claim 30 wherein said compound is at least one compound selected from the group consisting of N-{2-(4-(2-methoxyethyl)-2-methylphenoxy)-ethyl}-4-chloro-1,3-dimethyl-5-pyrazolecarboxamide, N-{2-(4-(2-ethoxyethyl)-2-methylphenoxy)-ethyl}-4-chloro-1,3-dimethyl-5-pyrazolecarboxamide, N-{2-(4-(2-n-propoxyethyl)-2-methylphenoxy)-ethyl}-4-chloro-1,3-dimethyl-5-pyrazolecarboxamide, N-{2-(4-(2-allyloxyethyl)-2-methylphenoxy)-ethyl}-4-chloro-1,3-dimethyl-5-pyrazolecarboxamide, N-{2-(4-(2-propargyloxyethyl)-2-methylphenoxy)-ethyl}-4-chloro-1,3-dimethyl-5-pyrazolecarboxamide, N-{2-(4-(2-ethoxyethyl)-2,6-dimethylphenoxy)-ethyl}-4-bromo-1,3-dimethyl-5-pyrazolecarboxamide, N-{2-(4-(2-ethoxyethyl)-2-methylphenoxy)-ethyl}-4-bromo-1,3-dimethyl-5-pyrazolecarboxamide, N-{2-(4-(2-ethoxyethyl)-2-methylphenoxy)-ethyl}-4-chloro-1-methyl-3-ethyl-5-pyrazolecarboxamide, N-{2-(4-(2-methoxyethyl)-2-methylphenoxy)-ethyl}-4-bromo-1-methyl-3-ethyl-5-pyrazolecarboxamide, N-{2-(4-(2-propargyloxyethyl)-2-methylphenoxy)-ethyl}-4-chloro-1-methyl-3-ethyl-5-pyrazolecarboxamide, N-{2-(4-(2-ethoxyethyl)-2,6-dimethylphenoxy)-ethyl}-4-chloro-1-methyl-3-ethyl-5-pyrazolecarboxamide and N-{2-(4-ethoxymethylphenoxy)-ethyl)-4-bromo-1-methyl-3-ethyl-5-pyrazolecarboxamide.

32. The method according to claim 30, wherein the compound is selected from the group consisting of N-(2-(4-n-pentyl-2-methylphenoxy)ethyl)-4-chloro-1,3-dimethyl-5-pyrazolecarboxamide and N-(2-(4-allyl-2-methylphenoxy)ethyl)-4-bromo-1,3-dimethyl-5-pyrazolecarboxamide.

* * * * *

UNITED STATES PATENT AND TRADEMARK OFFICE
CERTIFICATE OF CORRECTION

PATENT NO. : 5,039,692
DATED : August 13, 1991
INVENTOR(S) : OBATA et al It is certified that error appears in the above-identified patent and that said Letters Patent is hereby corrected as shown below:

Columns 5 and 6, under the heading "TABLE 1", replace the structural formula with

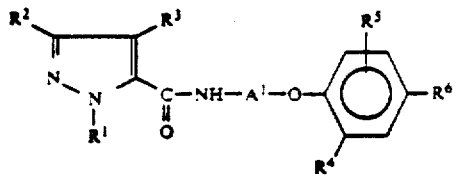

Columns 7 and 8, at the top of the page under the heading "TABLE 1-continued", replace the structural formula with

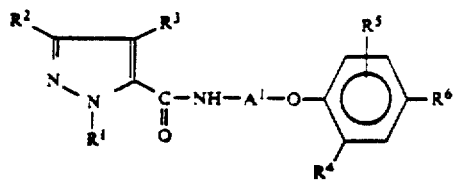

Signed and Sealed this

Seventh Day of December, 1993

Attest:

BRUCE LEHMAN

*Attesting Officer*    Commissioner of Patents and Trademarks